(12) United States Patent
Thomenius et al.

(10) Patent No.: US 7,257,051 B2
(45) Date of Patent: Aug. 14, 2007

(54) INTEGRATED INTERFACE ELECTRONICS FOR RECONFIGURABLE SENSOR ARRAY

(75) Inventors: Kai E. Thomenius, Clifton Park, NY (US); Rayette Ann Fisher, Niskayuna, NY (US); Robert Gideon Wodnicki, Niskayuna, NY (US); William Edward Burdick, Jr., Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 381 days.

(21) Appl. No.: 10/977,930

(22) Filed: Oct. 29, 2004

(65) Prior Publication Data

US 2005/0094490 A1  May 5, 2005

Related U.S. Application Data

(63) Continuation-in-part of application No. 10/383,990, filed on Mar. 6, 2003, now Pat. No. 6,865,140.

(51) Int. Cl.
*H04R 17/00* (2006.01)
*A61B 8/00* (2006.01)

(52) U.S. Cl. ............... 367/153; 367/105; 367/181; 600/447; 600/459

(58) Field of Classification Search ............... 367/105, 367/153, 178, 181; 600/447, 459
See application file for complete search history.

(56) References Cited

U.S. PATENT DOCUMENTS 4,641,660 A   2/1987   Bele 5,146,435 A   9/1992   Bernstein
5,452,268 A   9/1995   Bernstein (Continued)

FOREIGN PATENT DOCUMENTS

WO      WO 00/05001      3/2000

OTHER PUBLICATIONS

Ladabaum et al., Surface Micromachined Capacitive Ultrasonic Transducers, IEEE Trans. Ultrasonics, Ferroelectrics and Frequency Control, vol. 45, No. 3, May 1998, pp. 678-690.

(Continued)

*Primary Examiner*—Ian J. Lobo
(74) *Attorney, Agent, or Firm*—Fletcher Yoder

(57) ABSTRACT

An integrated switch matrix for reconfiguring subelements of a mosaic sensor array to form elements. The configuration of the switch matrix is fully programmable. The switch matrix includes access switches that connect subelements to bus lines and matrix switches that connect subelements to subelements. Each subelement has a unit switch cell comprising at least one access switch, at least one matrix switch, a respective memory element for storing the future state of each switch, and a respective control circuit for each switch. The access and matrix switches are of a type having the ability to memorize control data representing the current switch state of the switch, which control data includes a data bit input to turn-on/off circuits incorporated in the control circuit. The sensor array and the switching matrix may be built in different strata of a co-integrated structure or they may be built on separate wafers that are electrically connected. If the sensors are arranged on a hexagonal grid, the unit switch cells may be arranged on either a hexagonal or rectangular grid.

33 Claims, 13 Drawing Sheets

U.S. PATENT DOCUMENTS

| | | | |
|---|---|---|---|
| 5,558,623 | A | 9/1996 | Cody |
| 5,569,968 | A | 10/1996 | Lal et al. |
| 5,596,222 | A | 1/1997 | Bernstein |
| 5,619,476 | A | 4/1997 | Haller et al. |
| 5,684,324 | A | 11/1997 | Bernstein |
| 5,732,706 | A | 3/1998 | White et al. |
| 5,870,351 | A | 2/1999 | Ladabaum et al. |
| 5,894,452 | A | 4/1999 | Ladabaum et al. |
| 5,902,241 | A | 5/1999 | Seyed-Bolorforosh et al. |
| 5,982,709 | A | 11/1999 | Ladabaum et al. |
| 6,004,832 | A | 12/1999 | Haller et al. |
| 6,120,449 | A * | 9/2000 | Snyder et al. ............ 600/447 |
| 6,292,435 | B1 | 9/2001 | Savord et al. |
| 6,320,239 | B1 | 11/2001 | Eccardt et al. |
| 6,325,757 | B1 | 12/2001 | Erikson et al. |
| 6,328,697 | B1 | 12/2001 | Fraser |
| 6,359,367 | B1 | 3/2002 | Sumanaweera et al. |
| 6,381,197 | B1 | 4/2002 | Savord et al. |
| 6,384,516 | B1 | 5/2002 | Fraser |
| 6,443,901 | B1 | 9/2002 | Fraser |
| 6,503,204 | B1 | 1/2003 | Sumanaweera et al. |
| 6,571,445 | B2 | 6/2003 | Ladabaum |
| 6,585,653 | B2 | 7/2003 | Miller |
| 6,589,180 | B2 * | 7/2003 | Erikson et al. ............ 600/459 |
| 6,736,779 | B1 | 5/2004 | Sano et al. |
| 2002/0048219 | A1 | 4/2002 | Ladabaum et al. |
| 2005/0169107 | A1 | 8/2005 | Thomenius et al. |

OTHER PUBLICATIONS

Dietz et al., Wideband Annular Array Response 1978 Ultrasonics Symp. Proc., pp. 206-211.

Bailey et al., A Computer-Controlled Transducer for Real-Time Three Dimensional Imaging, Acoustical Imaging, vol. 18, Editors: Lee and Wade, Plenum Press, New York, 1991, pp. 543-551.

Ergun et al., Fabrication and Characterization of 1- Dimensional and 2- Dimensional CMUT Arrays etc., IEEE, 2002, pp. 2361-2367.

Orallean et al., Capacitive Micromachined Ultrasonic Transducers: Next-Generation Arrays for Acoustic Imaging, IEEE Trans. Ultrasonics, Ferroelectronics and Freq. Control, vol. 29, No. 11, Nov. 2002, pp. 1596-1610.

Jin et al., Micromachined Capacitive Ultrasonic Immersion Transducer for Medical Imaging, Proc. 20th Annual Int'l Conf. IEEE Engineering in Medicine and Biology Society, vol. 20, No. 2, 1998, pp. 779-782.

* cited by examiner

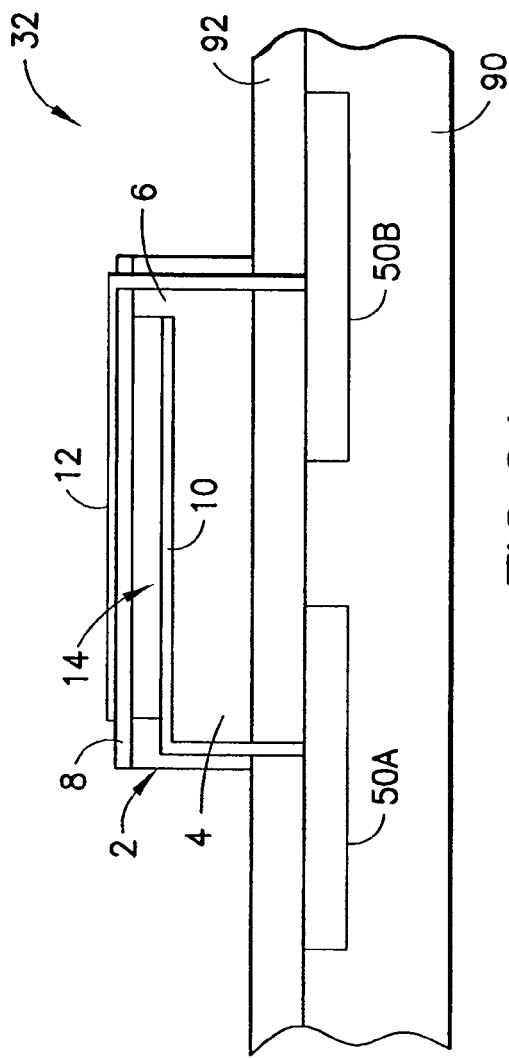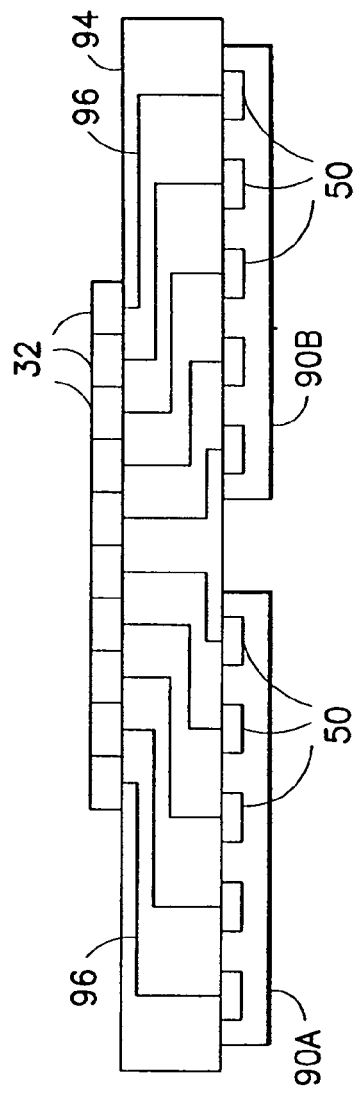

INTEGRATED INTERFACE ELECTRONICS FOR RECONFIGURABLE SENSOR ARRAY

RELATED PATENT APPLICATION

This application is a continuation-in-part of and claims priority from U.S. patent application Ser. No. 10/383,990 filed on Mar. 6, 2003, now U.S. Pat No. 6,865,140, and entitled "Mosaic Arrays Using Micromachined Ultrasound Transducers".

STATEMENT REGARDING FEDERALLY SPONSORED RESEARCH AND DEVELOPMENT

The United States Government may have certain rights in this invention pursuant to U.S. Government Contract Number DAMD17-02-1-0181 awarded by the U.S. Army.

BACKGROUND OF THE INVENTION

This invention generally relates to reconfigurable arrays of sensors (e.g., optical, thermal, pressure, ultrasonic). In particular, the invention relates to reconfigurable micromachined ultrasonic transducer (MUT) arrays. One specific application for MUTs is in medical diagnostic ultrasound imaging systems. Another specific example is for non-destructive evaluation (NDE) of materials, such as castings, forgings, or pipelines.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is continuously refocused along the scan line as the reflected ultrasonic waves are received.

For ultrasound imaging, the array typically has a multiplicity of transducers arranged in one or more rows and driven with separate voltages in transmit. By selecting the time delay (or phase) and amplitude of the applied voltages, the individual transducers in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers is desirable for both two- and three-dimensional imaging applications. The ultrasound transducers are typically located in a hand-held transducer probe that is connected by a flexible cable to an electronics unit that processes the transducer signals and generates ultrasound images. The transducer probe may carry both ultrasound transmit circuitry and ultrasound receive circuitry.

A reconfigurable ultrasound array is one that allows groups of subelements to be connected together dynamically so that the shape of the resulting element can be made to match the shape of the wave front. This can lead to improved performance and/or reduced channel count. Reconfigurability can be achieved using a switching network.

Recently semiconductor processes have been used to manufacture ultrasonic transducers of a type known as micromachined ultrasonic transducers (MUTs), which may be of the capacitive (MUT) or piezoelectric (pMUT) variety. MUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. One advantage of MUTs is that they can be made using semiconductor fabrication processes, such as microfabrication processes grouped under the heading "micromachining". The systems resulting from such micromachining processes are typically referred to as "micromachined electromechanical systems (MEMS). As explained in U.S. Pat. No. 6,359,367:

> Micromachining is the formation of microscopic structures using a combination or subset of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein.

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A cMUT cell is the term used to describe a single one of these hexagonal "drum" structures. The cMUT cells can be very small structures. Typical cell dimensions are 25–50 microns from flat edge to flat edge on the hexagon. The dimensions of the cells are in many ways dictated by the designed acoustical response. It may not be possible to create larger cells that still perform well in terms of frequency response and sensitivity desired.

Unfortunately, it is difficult to produce electronics that would allow individual control over such small cells. While in terms of the acoustical performance of the array as whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form rings or elements by connecting subelements together using a switching network. The elements can be reconfigured by changing the state of the switching network. However, subelements comprise connected cells that are not switchably disconnectable and thus cannot be reconfigured. All of the following analysis is also valid if the array is made of PZT or some other more common or future transducer technology.

Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays and leads to the annular array concept. The reconfigurability can be used to step the beam along the larger underlying two-dimensional transducer array in order to form a scan or image. The reconfigurability might also be used to improve performance for multiple transmit applications by assigning more channels to the smaller active aperture in the near field. There are many other applications where reconfigurability might prove useful.

In a mosaic annular transducer array and other mosaic transducer arrays, a large number of ultrasound transducer subelements must be connected together using a distributed switch matrix. The subelements build up larger elements that are used for transmission and reception of ultrasound signals. The configuration of the elements and therefore the subelements changes each time that a new line of data or "view" is acquired. Each time that the configuration changes, the state (on or off) of all of the switches in the switching matrix must be updated to create the required interconnections that build up the new state of the elements and subelements.

In a reconfigurable sensor array, a large number of sensor subelements must be accessed by system electronics. This presents a significant bottleneck in terms of routing of signal and control lines to associated system processing electronics.

In current high-channel-count systems, connections to individual sensor elements are brought out using individual flexible wires and routed to external printed circuit boards housing the necessary scanning electronics. The wiring and printed circuit boards are bulky and not currently applicable to a very large number of transducer subelements as is the case in a mosaic transducer array.

Reconfigurable ultrasound arrays require a complex switching network that may be difficult or impossible to implement with currently available electronics. There is a need for a simplified switching network that has application in arrays of ultrasonic transducer subelements as well as in arrays of other types of sensors (e.g., optical, thermal, pressure). There is also a need for a construction comprising integrated switching electronics disposed beneath the sensor array for rapidly reconfiguring the sensor array.

BRIEF DESCRIPTION OF THE INVENTION

The invention is directed to an integrated switch matrix for reconfiguring subelements of a mosaic sensor array. The configuration of the switch matrix is fully programmable. The switch matrix includes access switches that connect subelements to bus lines and matrix switches that connect subelements to subelements. Each subelement has a unit switch cell associated therewith. In one embodiment, each unit switch cell comprises at least one access switch, at least one matrix switch, a respective pair of latches for storing the future state of each switch, and a respective control circuit for each switch. The access and matrix switches are of a type having the ability to memorize control data representing the current switch state of the switch, which control data includes one data bit input to turn-on/off and turn-off circuits incorporated in the control circuit. The sensors may be optical, thermal or pressure sensors or ultrasonic transducers. The sensor array and the switching matrix may be built in different strata of a co-integrated structure or they may be built on separate wafers that are electrically connected. It may also be possible to build the sensors in the same strata as the electronics; however, this would decrease the amount of area available to the electronics and is therefore less desirable. If the sensors are arranged on a hexagonal grid, the unit switch cells may be arranged on either a hexagonal or rectangular grid.

The embodiments disclosed herein use a two-dimensional array of capacitive micromachined ultrasound transducers (cMUTs) as the underlying grid from which larger elements are constructed. The present invention is not limited, however, to cMUT structures and is equally applicable to other conventional or future transducer technologies.

One aspect of the invention is a device comprising: a multiplicity of sensors arranged along a first set of substantially parallel lines in a first stratum; a multiplicity of unit electronics cells arranged along a second set of substantially parallel lines in a second stratum, the first and second sets of lines being substantially mutually parallel and aligned with each other; and a multiplicity of electrical connections, each of the electrical connections electrically connecting a respective one of the unit electronics cells to a respective one of the sensors, wherein each of the unit electronics cells comprises: a respective plurality of switches for closing respective pathways to a respective connection point that is electrically connected to a respective sensor and that is not switchably disconnectable from the respective sensor; and a respective control circuit for controlling the switch states of the switches.

Another aspect of the invention is a device comprising a multiplicity of sensors built in or on a first substrate; a multiplicity of unit electronics cells integrated in a second substrate disposed adjacent to and confronting the first substrate; a multiplicity of bus lines supported by the second substrate; and a multiplicity of electrical connections disposed between the first and second substrates, each of the electrical connections electrically connecting a respective one of the unit electronics cells to a respective one of the sensors, wherein each of the unit electronics cells comprises a respective plurality of switches and a respective control circuit for controlling the switch states of the switches, each plurality of switches comprising an access switch that connects the associated sensor with one of the bus lines when the access switch is turned on, and a matrix switch that connects a sensor associated with a neighboring unit electronics cell to the one bus line via the access switch when the access switch and the matrix switch of the unit electronics cell are turned on.

A further aspect of the invention is a device comprising: a multiplicity of ultrasonic transducer subelements arranged in a first stratum, each subelement comprising a respective plurality of cMUT cells that are electrically interconnected with each other and are not switchably disconnectable from each other; a multiplicity of unit CMOS electronics cells arranged along a second stratum that underlies the first stratum; a multiplicity of bus lines; and a multiplicity of electrical connections, each of the electrical connections electrically connecting a respective one of the unit CMOS electronics cells to a respective one of the ultrasonic transducer subelements, wherein each of the unit CMOS electronics cells comprises a respective plurality of switches and a respective control circuit for controlling the switch states of the switches, each plurality of switches comprising an access switch that connects the associated ultrasonic transducer subelement with one of the bus lines when the access switch is turned on, and a matrix switch that connects an ultrasonic transducer subelement associated with a neighboring unit CMOS electronics cell to the one bus line via the access switch when the access switch and the matrix switch of the unit CMOS electronics cell are turned on.

Other aspects of the invention are disclosed and claimed below.

BRIEF DESCRIPTION OF THE DRAWINGS

FIG. 21 is a drawing showing a representative cMUT cell with top and bottom electrodes connected to an electronics layer by metallized vias.

FIG. 22 is a drawing showing an embodiment of the invention wherein metal routing between the sensor and electronics planes includes rerouting that allows use of an electronics chip that is larger than the sensor array.

Reference will now be made to the drawings in which similar elements in different drawings bear the same reference numerals.

DETAILED DESCRIPTION OF THE INVENTION

The invention is directed to a reconfigurable sensor array having an integrated switching matrix. For purposes of illustration, the reconfigurable array will be described with reference to capacitive micromachined ultrasonic transducers (cMUTs). However, it should be understood that the aspects of the invention disclosed herein are not limited in their application to probes employing cMUTs, but rather may also be applied to probes that employ pMUTs or even diced piezoceramic arrays where each of the diced subelements are connected by interconnect means to an underlying switching layer. The same aspects of the invention also have application in reconfigurable arrays of optical, thermal or pressure sensors.

Figure 1:
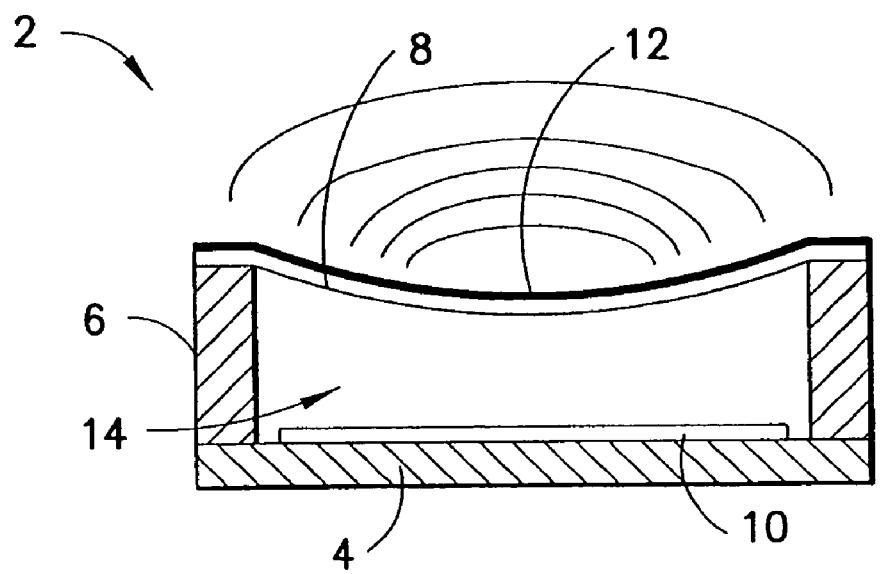
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as whole, the small cell size is excellent and leads to great flexibility, control is limited to larger structures. Grouping together multiple cells and connecting them electrically allows one to create a larger subelement, which can have the individual control while maintaining the desired acoustical response. One can form rings or elements by connecting subelements together using a switching network. The elements can be reconfigured by changing the state of the switching network. However, individual subelements cannot be reconfigured to form different subelements.

MUT cells can be connected together (i.e., without intervening switches) in the micromachining process to form subelements. The term "acoustical subelement" will be used in the following to describe such a cluster. These acoustical subelements will be interconnected by microelectronic switches to form larger elements by placing such switches within the silicon layer or on a different substrate situated directly adjacent to the transducer array. This construction is based on semiconductor processes that can be done with low cost in high volume.

As used herein, the term "acoustical subelement" is a single cell or a group of electrically connected cells that cannot be reconfigured, i.e., the subelement is the smallest independently controlled acoustical unit. The term "subelement" means an acoustical subelement and its associated integrated electronics. An "element" is formed by connecting subelements together using a switching network. The elements can be reconfigured by changing the state of the switching network. At least some of the switches included in the switching network are part of the "associated integrated electronics", as explained in greater detail below.

Figure 2:
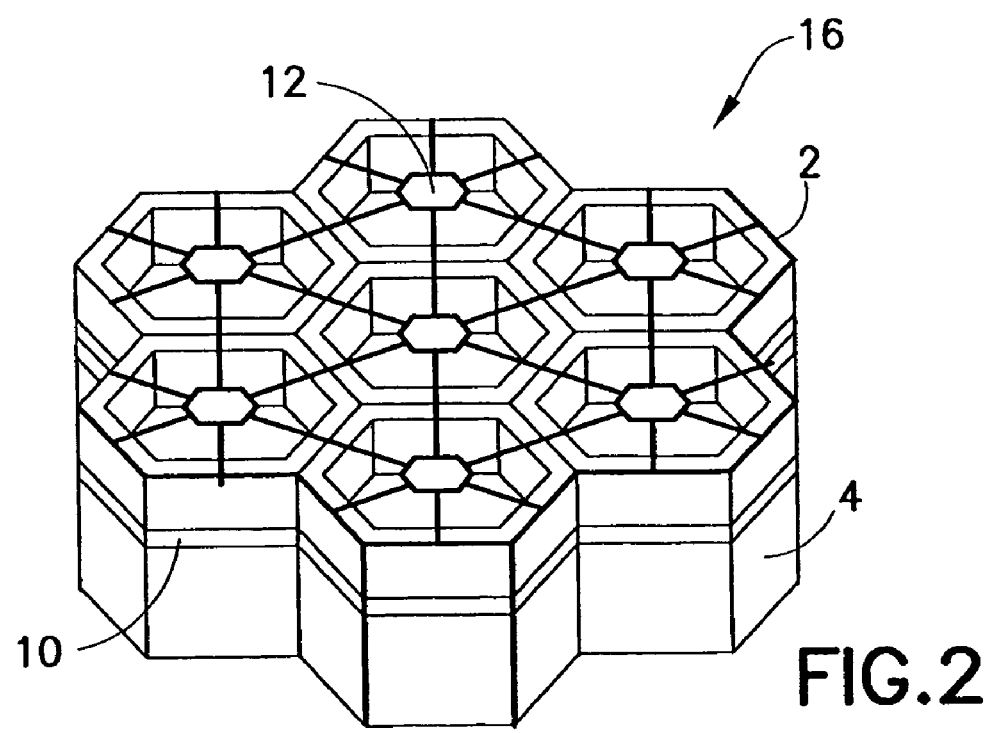
FIG. 2 is a drawing showing a "daisy" subelement formed from seven hexagonal MUT cells having their top and bottom electrodes respectively connected together without intervening switches. This drawing is taken from U.S. patent application Ser. No. 10/383,990.

For the purpose of illustration, FIG. 2 shows a "daisy" transducer subelement 16 made up of seven hexagonal cMUT cells 2: a central cell surrounded by a ring of six cells, each cell in the ring being contiguous with a respective side of the central cell and the adjoining cells in the ring. The top electrodes 12 of each cMUT cell 2 are electrically coupled together by connections that are not switchably disconnectable. In the case of a hexagonal array, six conductors radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger capacitive transducer subelement 16.

Subelements of the type seen in FIG. 2 can be arranged to form a two-dimensional array on a semiconductive (e.g., silicon) substrate. These subelements can be reconfigured to form elements, such as annular rings, using a switching network. Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays. The reconfigurability can be used to step the beam along the larger underlying two-dimensional transducer array in order to form a scan or image.

Figure 3:
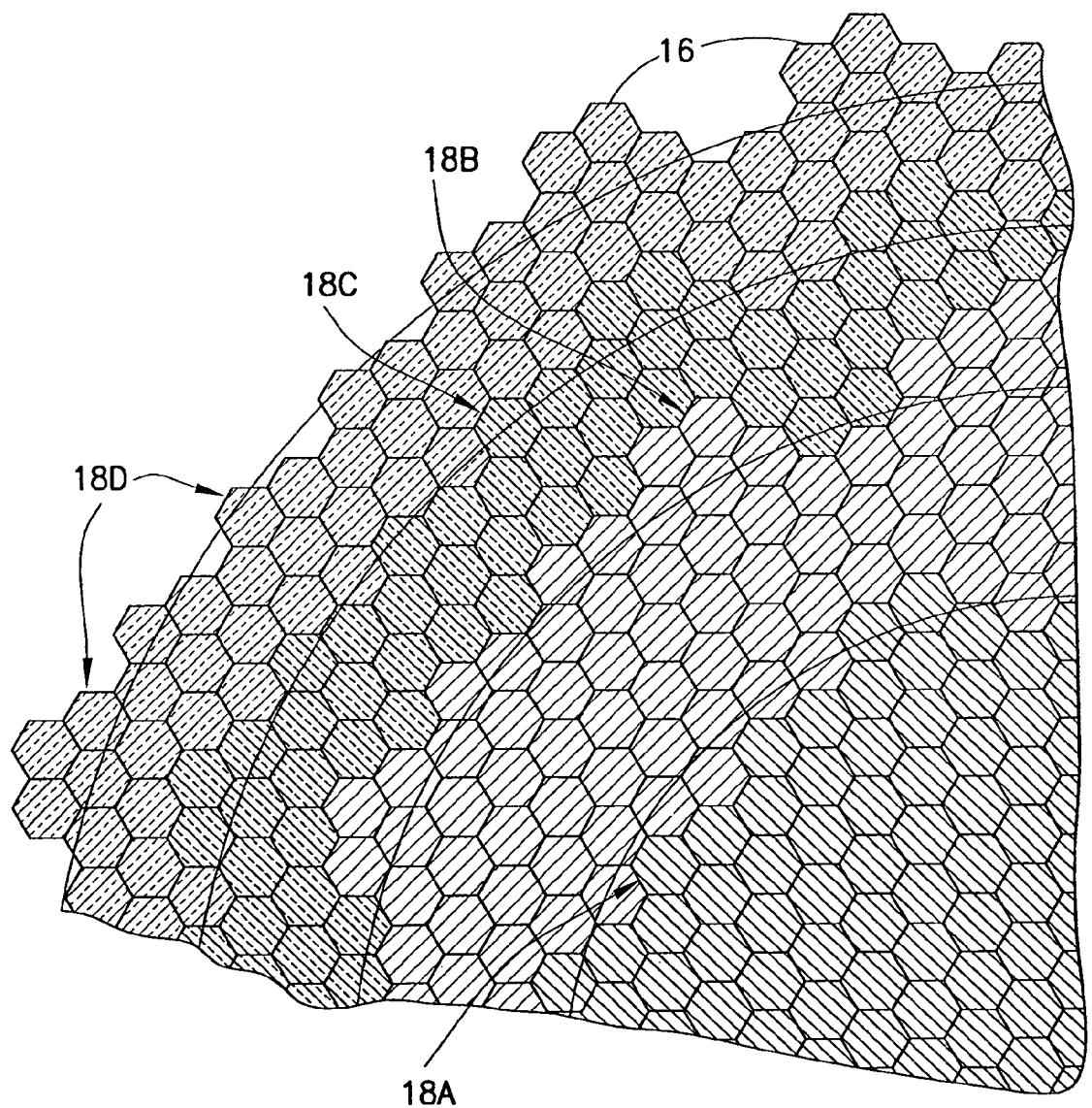
FIG. 3 is a drawing showing a sector of a mosaic array comprising four annular elements as disclosed in U.S. patent application Ser. No. 10/383,990, each element consisting of a tessellation of "daisy" subelements configured to have approximately equal area per element.

There are numerous ways in which one can form transducer arrays using MUT cells and acoustical subelements. FIG. 3 shows one example of tessellations of acoustical subelements to form a mosaic array. In the embodiment shown in FIG. 3, four approximately annular elements (referenced by numerals 18A–D respectively), each comprising a tessellation of "daisy" acoustical subelements (seven MUT cells connected together per subelement), are configured to have approximately equal area per element. The tessellation in each case can be made up of multiple subelement types. The array pattern need not be a tessellation, but can have areas without acoustical subelements. For instance, there could be vias to bring top electrode connections of the acoustical subelement or cells below the array.

The configurations of the invention can be changed to optimize various acoustic parameters such as beamwidth, side lobe level, or depth of focus. Alternatively, the acoustical subelements could be grouped to form one aperture for the transmit operation and immediately switched to another aperture for the receive portion. While FIG. 3 shows respective portions of approximately annular elements, other configurations can be implemented, for example, non-continuous rings, octal rings, or arcs. The choice of pattern will depend on the application needs.

Most apertures will consist of contiguous grouped subelements interconnected to form a single larger element, such as the annular elements shown in FIG. 3. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections.

Given a particular geometry, the reconfigurable array maps acoustical subelements to system channels. This mapping is designed to provide improved performance. The mapping is done through a switching network, which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate. For a PZT or more conventional implementation, the switch network would simply be fabricated in a separate silicon substrate and attached to the PZT array.

Figure 4:
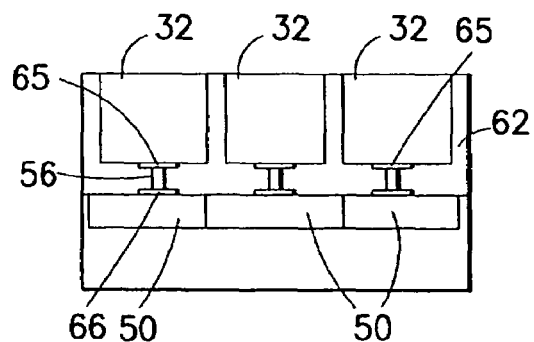
FIG. 4 is a drawing showing a cross-sectional view of a co-integrated cMUT and application specific integrated circuit (ASIC) array.

A cross-sectional view of a co-integrated cMUT and ASIC array is shown in FIG. 4 to illustrate how the connections would be made from the ASIC to the cMUTs. As shown, a single via 56 is used to connect each cMUT subelement 32 to its counterpart CMOS subelement (or "cell") 50. The vias 56, which connect the pads 65 of the signal electrodes to respective conductive pads 66 formed on the switch ASIC, may be embedded in an acoustic backing layer 62 or other suitable insulating material.

FIG. 21 shows portions 50A and 50B of an electronics cell formed in a substrate 90, which is separated from a cMUT subelement 32 by a passivation layer 92. Only one cMUT cell 2 of subelement 32 is shown, but it should be appreciated that each subelement comprises more than one cMUT cell connected together in a manner that is not switchably disconnectable. As shown in FIG. 21, it may be desirable to have more than one signal per subelement. In particular, both the top electrode 12 and the bottom electrode 10 can be brought down to the electronics cell, e.g., by means of metallized vias that pass through the passivation layer 92. This provides independent control of both faces of the cMUT subelement, which can be used to independently bias all cMUT subelements in the array at different bias voltages. This feature could be used, for example, to reverse the polarity of the transmit pulse or to adjust for slight variations in cMUT sensitivity from subelement to subelement.

Figure 5:
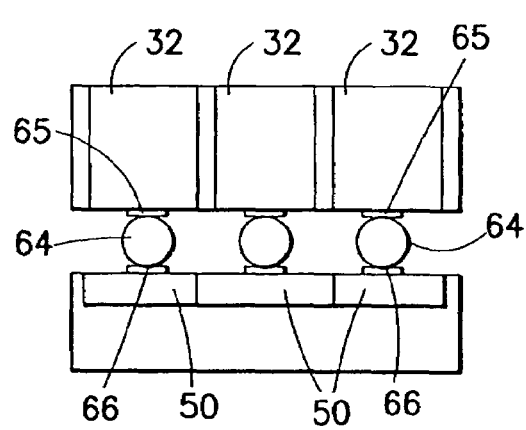
FIG. 5 is a drawing showing a cross-sectional view of a cMUT device substrate connected to an ASIC switch matrix.

It is also possible to build the cMUTs on a separate substrate (e.g., a wafer) and connect them to the ASIC switch matrix separately, as shown in FIG. 5. Here for example, electrically conductive bumps 64 and electrically conductive pads 65, 66 are used to connect the individual cMUT subelements 32 to their switch electronics counterparts 50. Other interconnect techniques such as anisotropic conductive paste (ACP), anisotropic conductive film (ACF), electrically conductive polymers, metallized bumps, vertical interconnect systems, e.g., z-axis interposers, flexible printed circuits, etc. or metallized vias could also be used.

Figure 6:
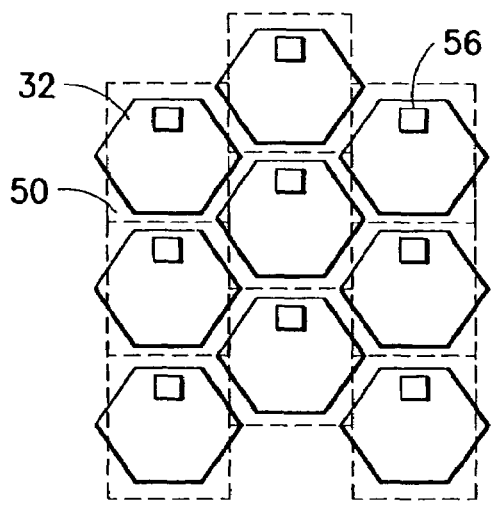
FIG. 6 is a drawing showing a top view of a hexagonal array of cMUT subelements atop a hexagonal array of associated unit switch cells.
Figure 7:
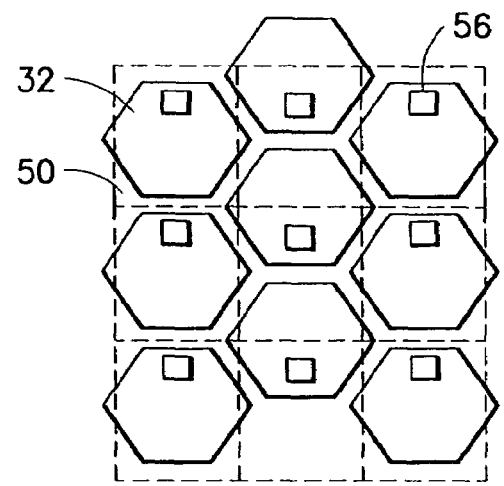
FIG. 7 is a drawing showing a top view of a hexagonal array of cMUT subelements atop a rectangular array of associated unit switch cells.

For optimum packing density it is useful to tile the cMUT subelements 32 and the associated electronics on a hexagonal grid as illustrated in FIG. 6, which shows a top view of the ASIC switch matrix. Here the CMOS unit switch cells 50 are disposed in columns where every second column is offset by half a cell height. With proper choice of the cell dimensions, this will yield a perfect hexagonal array of pads 66 as shown. The vias 56 (also arranged in a hexagonal array) then connect to the respective pads (not shown in FIG. 4) that form the basis of connections to the transducer layer above, comprising a hexagonal array of subelements. A more straightforward ASIC implementation is illustrated in FIG. 7. Here the CMOS unit switch cells 50 are arranged in horizontal rows and vertical columns to form a rectangular grid, while the hexagonal subelements 32 above them form a hexagonal grid. As shown in FIG. 7, the unit switch cell pads 66, arranged in rows and columns to form a rectangular array, still line up correctly to produce the connections such that the unit switch cells 50 are electrically connected to respective hexagonal subelements 32. In either case, the hexagonal grid pattern of the subelements makes it possible to realize the mosaic annular array beam patterns as shown in FIG. 3.

Figure 8:
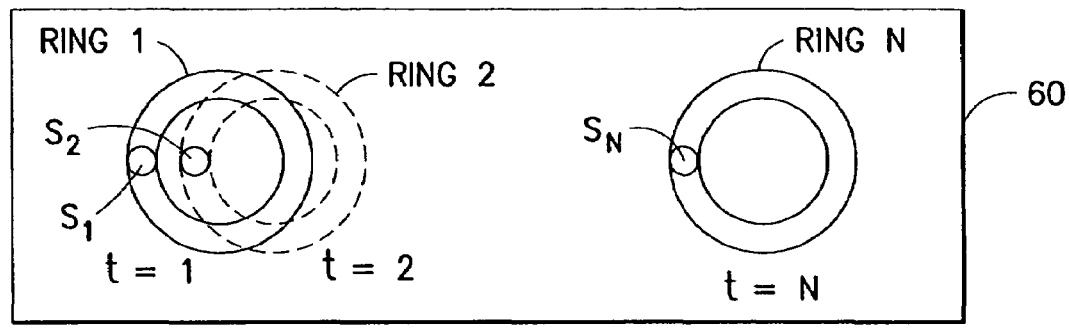
FIG. 8 is a drawing showing translation of an annular transducer element across an array.

In typical operation, the reconfigurable array is programmed with an initial aperture pattern similar to the one shown in FIG. 3. This pattern allows the beamformer to create a beam in front of the array. During imaging, the aperture is scanned across the array 60 as illustrated in FIG. 8, where the ring goes from ring 1 at t=1 to ring 2 at t=2 and finally ring N at t=N, where t is time and N is a positive integer greater than 2. In this way the beam is swept in space in front of the array and the beamformed echoes are used to build up successive lines of the image. The purpose of a reconfigurable array is to be able to accomplish the imaging operation illustrated in FIG. 8 electronically for an arbitrarily complex array pattern. Previous ultrasound scanners are capable of accomplishing electronic scanning but are limited in the complexity of the aperture due to lack of fine distribution of sensor subelements in the elevation direction and fixed geometry.

A fully reconfigurable array as illustrated in FIG. 8 presents a number of significant challenges in implementation. The sensor array is subdivided into tens of thousands of subelements. Beam patterns are built up by grouping the subelements in their connections to a finite number of system transmit/receive and beamforming channels. When used to implement the mosaic annular array concept, the reconfigurable array will form multiple rings that are translated across the array electronically. At each new step in the translation, the entire ring pattern is reprogrammed into the array to create a new configuration. One could also provide the ability to update ring patterns between transmit and receive and at multiple intervals during receive to reduce the distortion of the beam as formed, thereby improving the image quality.

In typical systems, 128 or more beamforming channels are used. Current ultrasound systems use multiplexing architectures that can route the 128 system channels to a fixed number of transducer elements. Using judicious design of these multiplexer networks, it is possible to create a standard scanning pattern with a limited amount of electronics. In most cases however, the scanning pattern is fixed and not reconfigurable due to the limitations of the network. A fully reconfigurable array does not suffer from these limitations; however, it requires a very dense switching matrix to implement it.

As is illustrated in FIG. 8, the fundamental nature of the reconfigurable array requires that any subelement can be arbitrarily connected to any system channel. For example, as the aperture is scanned from the first location to the next location, the subelement S2 first must be part of an internal ring (not shown) and then must be part of ring 2. This means that it must switch from being connected to a first system channel to being connected to a different system channel in a short period of time. This is generally true of a large number of subelements in the array during scanning operation.

Figure 9:
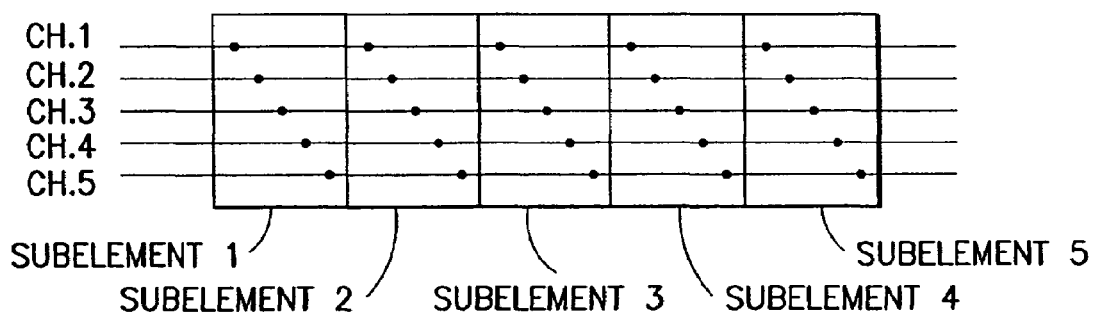
FIG. 9 is a drawing showing an architecture wherein all system channels are distributed throughout the array such that each transducer subelement has access to every system channel.

The simplest way to implement this requirement would be to distribute all system channels throughout the array such that each subelement has access to every system channel. This architecture is illustrated in FIG. 9. Here only five system channels are shown for illustration. Each system channel is bussed through every subelement with local switches used to select which system channel is picked up by which subelement.

In a system where the matrix electronics lie directly behind the transducer array, the space for each subelement's switching electronics is reduced to the size of the subelement. In typical ultrasound systems this size is on the order of a few hundred microns but could be smaller than this. Since the size of a switch varies inversely with its on resistance, one is faced with a tradeoff: more switches with higher on resistance or fewer switches with lower on resistance. Even taking the extreme case however, in which the switches are as small as they can be, it soon becomes apparent that with present semiconductor technologies, many more than 16 switches cannot fit readily in the allotted space. Since for a real array the fully populated architecture of FIG. 9 will contain still more switches, it appears to be intractable with the current state of the art.

Although future technologies may make it quite feasible to integrate many more switches in the same space, progress in ultrasound will tend to reduce the allotted cell size since it is related to the wavelength of the imager, which must shrink for improved image quality. In addition, many more components, such as digital control and transmit/receive circuits, will migrate into this same limited area. Therefore, the fully populated architecture, while attractive for its simplicity, is not immediately tenable or practicable.

Figure 10:
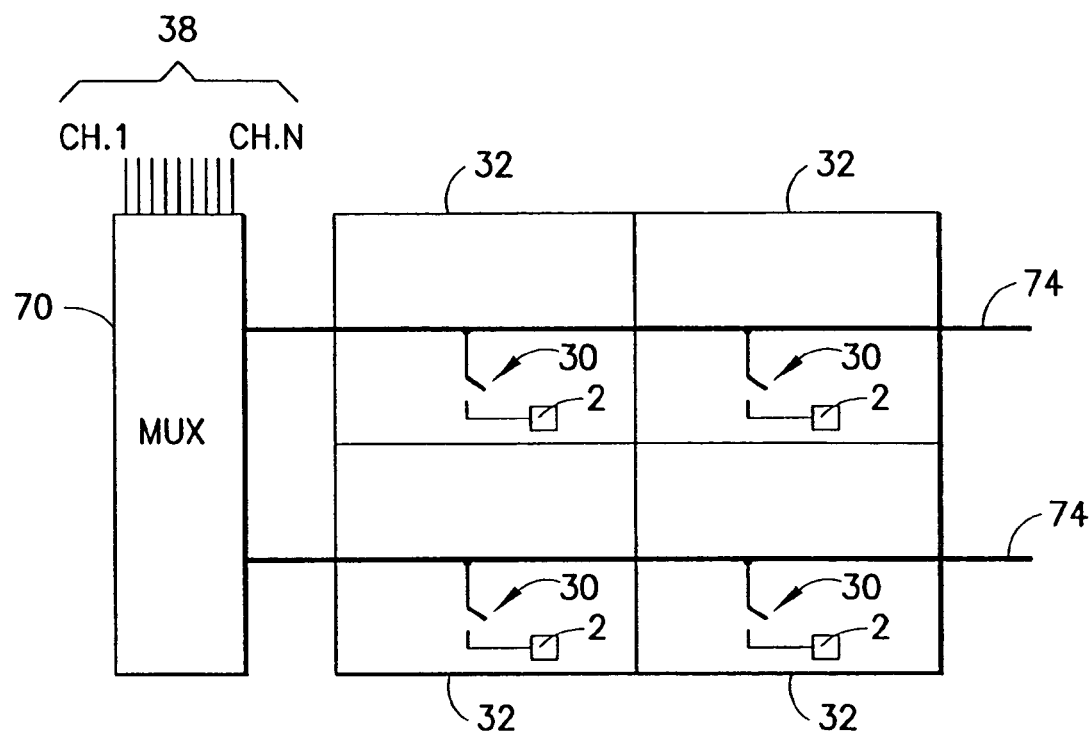
FIG. 10 is a drawing showing an architecture wherein the number of switches in each subelement is limited by having one bus line per row of subelements, the bus lines being connected to system channels via a multiplexer.
Figure 11:
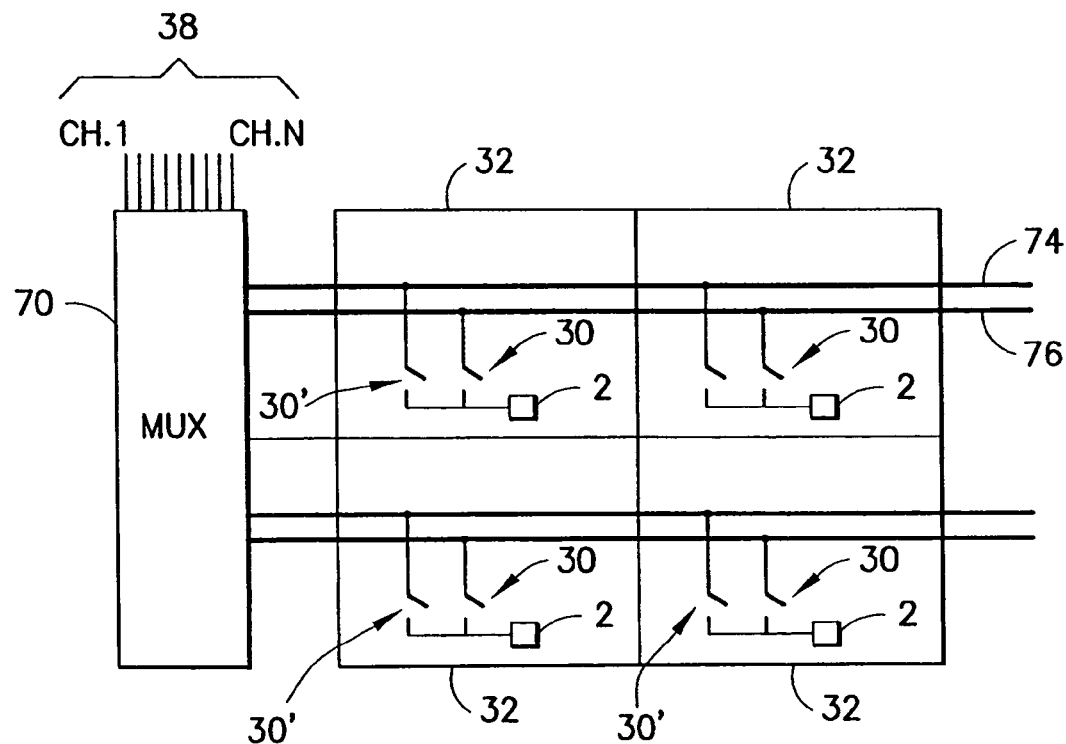
FIG. 11 is a drawing showing an architecture having multiple bus lines per row of subelements, making it possible to group subelements on different system channels within the same row.

A better solution to the interconnect problem described above is to limit the number of switches in each subelement while at the same time providing for the flexibility required in a reconfigurable array. This can be done by using a limited number of bus lines and making these reconfigurable, as is illustrated in FIG. 10. Here a multiplexer 70 is used to arbitrarily select any of the system channels 38 (CH.1 through CH. N) to be connected to any of the bus lines 74, with each row of subelements 32 served by only a single bus line. The cMUT cells 2 of each subelement (only one cMUT cell is shown for each subelement) are connected to a bus line by means of a respective access switch 30. A key feature of this architecture is that many of the switches are located outside of the array and therefore are not constrained by the geometry of the transducers. A one-dimensional pattern can be scanned across the array using this architecture by successively selecting which row of subelements is connected to which system channel. A further improvement to this architecture is shown in FIG. 11. Here multiple bus lines 74, 76 are routed down each row of subelements 32. The cMUT cells 2 of each subelement 32 can be connected either to bus line 74 via access switch 30' or to bus line 76 via access switch 30. This architecture provides flexibility in the horizontal direction since it is now possible to group subelements on different system channels within the same row.

Figure 12:
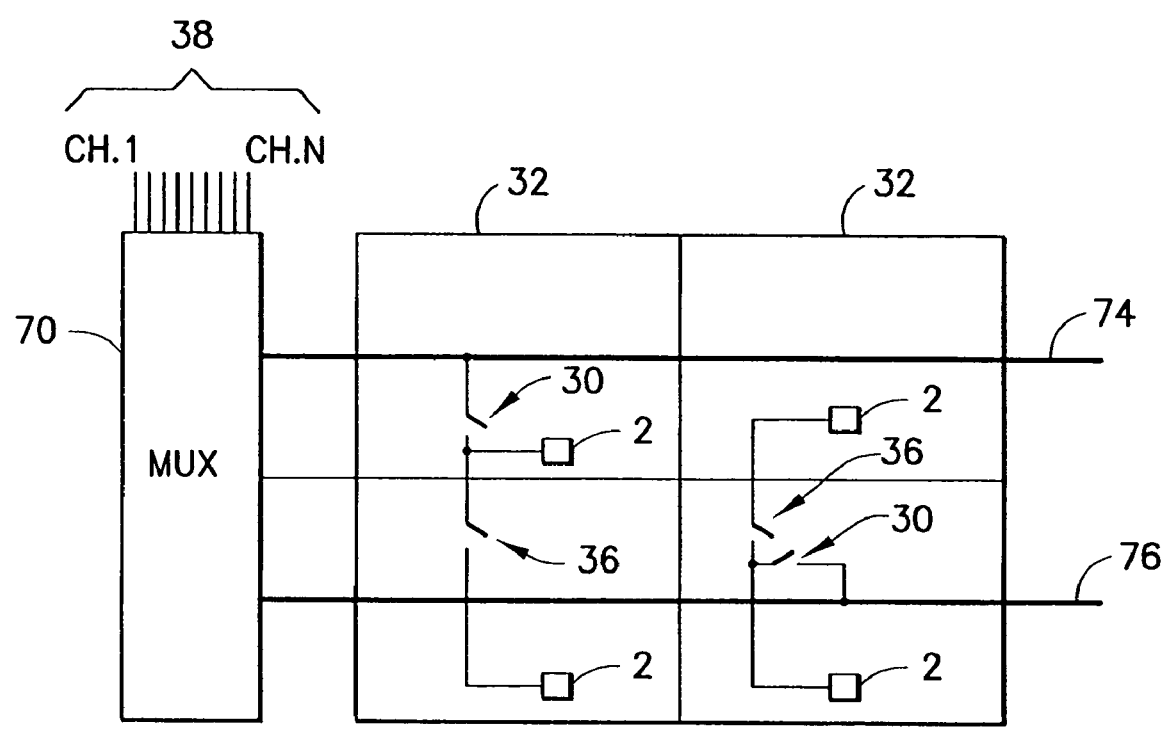
FIG. 12 is a drawing showing an architecture in accordance with one embodiment of the invention that allows a subelement in a first row to connect to a bus line for a second row of subelements by connecting to an access switch of an adjacent subelement in the second row via a matrix switch of the subelement in the first row.

A further improvement to the above architecture can be made by realizing that most apertures will consist of contiguous grouped subelements interconnected to form a single larger element. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections. This architecture is illustrated in FIG. 12. Here individual subelements 32 are able to connect to the bus line associated with their row by way of access switches 30 and are able to connect to the bus line associated with an adjacent row by way of matrix switches 36, which connect one subelement to an adjacent subelement.

Figure 13:
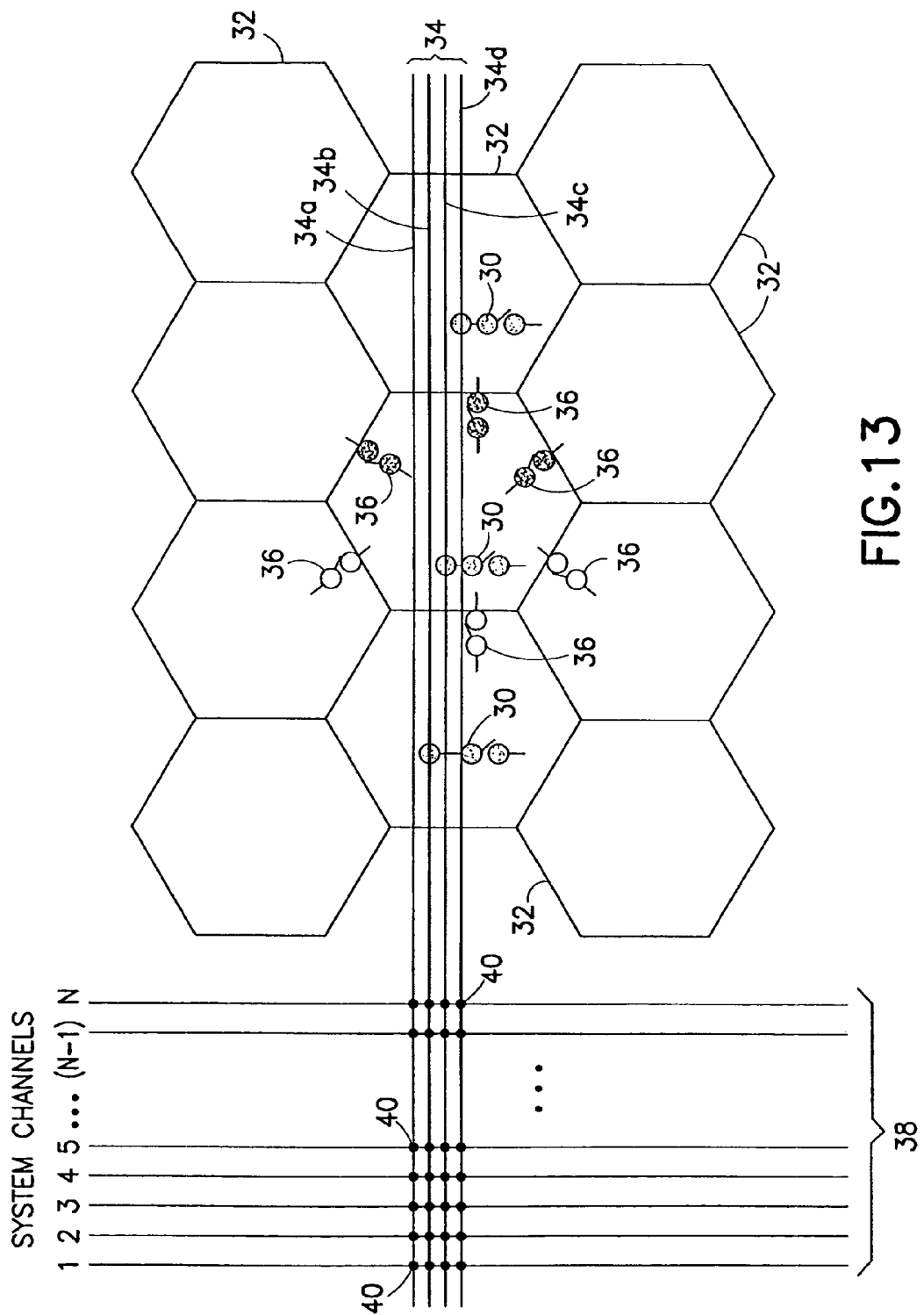
FIG. 13 is a drawing showing an architecture in accordance with another embodiment of the invention that allows a particular subelement in a particular row of a cMUT array to be connected to any one of a multiplicity of system channel bus lines.

One embodiment of the invention, shown in FIG. 13, incorporates all of the above-mentioned improvements together. Here an access switch 30 is used to connect a given subelement 32 to a row bus line of bus 34. This architecture is directly applicable to a mosaic annular array. In such a device multiple rings can be formed using the present architecture, wherein each ring is connected to a single system channel using one or more access switches, each of which is connected to a bus line, which is in turn connected to a system channel.

The access switches are staggered as shown in FIG. 13 to reduce the number required for a given number of bus lines, as discussed further below. Random ordering of access switches to bus lines (not shown) could also be employed to reduce artifacts due to the repeating patterns. More than one access switch in each subelement could be used to improve the flexibility of the array. In such an architecture, a tradeoff between flexibility and number of access switches per subelement would be made where the number is still significantly fewer than the number of bus lines and system channels. It is also possible to use more than one access switch per bus line in each element. This would improve the yield of the device since non-functioning access switches could be bypassed using the redundant access switches.

The row bus lines are connected to the system channels using a cross-point switching matrix as shown in FIG. 13. A sparse cross-point switch could be used as well in which fewer multiplexer switches would be required. Such an architecture would be more efficient in use of space but would require judicious choice of switch configurations to ensure that all bus lines could be properly connected. As shown in FIG. 12, multiple bus lines can be used per row. More bus lines improves flexibility of the array at the expense of more multiplexer switches and more routing area inside the array. It is possible to skip rows or to use different numbers of bus lines on different rows. For example, to conserve area it might be advantageous to share a group of bus lines between every pair of adjacent rows of subelements.

Figure 14:
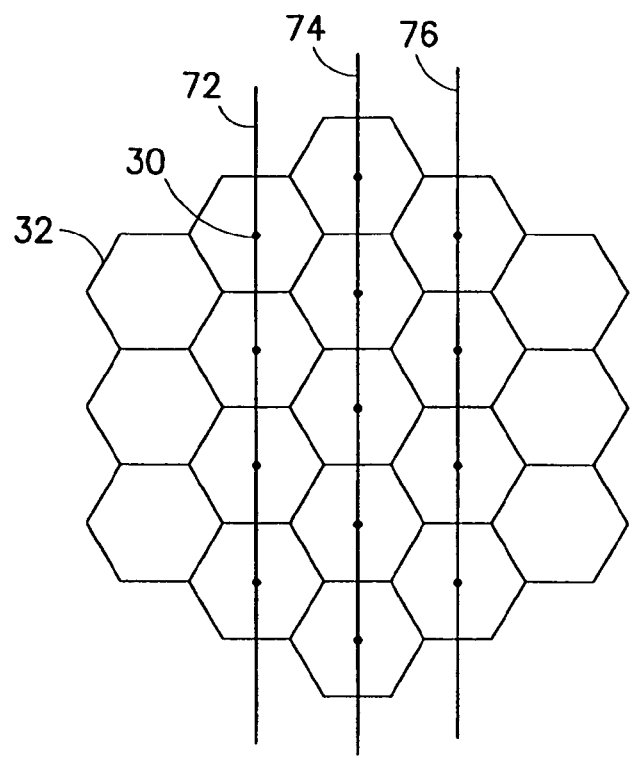
FIG. 14 is a drawing showing a hexagonal array of subelements with bus lines connected to respective columns of subelements via access switches (indicated by solid dots).
Figure 15:
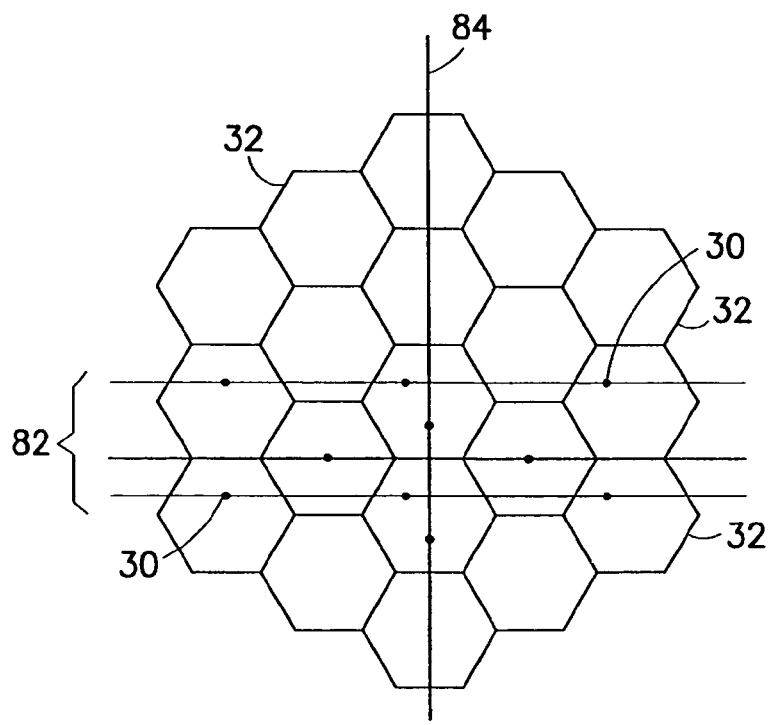
FIG. 15 is a drawing showing a hexagonal array of subelements with some subelements connected to vertical and horizontal bus lines via respective access switches (indicated by solid dots).
Figure 16:
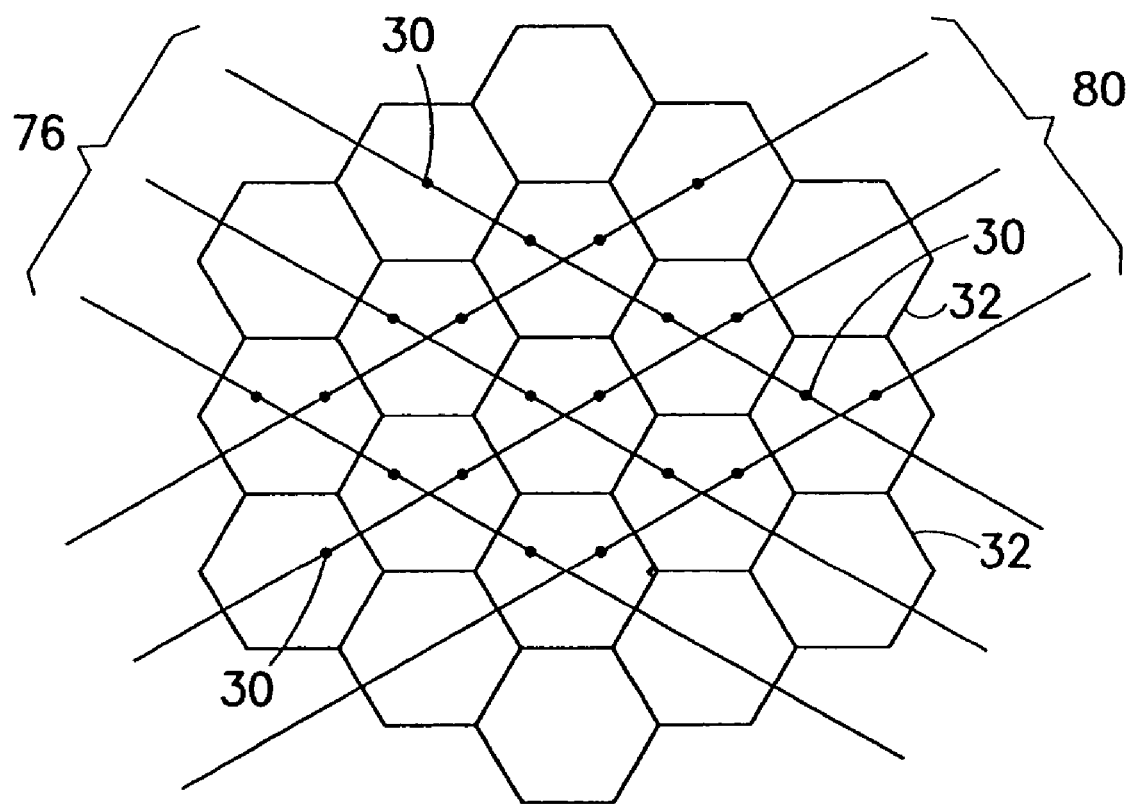
FIG. 16 is a drawing showing a hexagonal array of subelements with bus lines disposed diagonally along the natural axes of the hexagonal array. Access switches are indicated by solid dots.

Although only horizontal bus lines have been discussed thus far, it is also possible to dispose both vertically and horizontally running bus lines within an array. Bus lines could be disposed vertically as illustrated in FIG. 14 (see bus lines 72, 74, 76). Referring to FIG. 15, one set of bus lines 82 could be disposed horizontally and another set (only one bus line 84 is shown) disposed vertically. In this case each subelement or group of subelements will be connectable to a vertical bus line via one access switch and will further be connectable to a horizontal bus line via a different access switch. However, in the case where bus lines are run in both directions because the electronic real estate available for bus lines is running low and more bus lines are needed, but there is still only a single access switch in a subelement, then each subelement's access switch could be connected to either the horizontal bus line or the vertical bus line and not both. Finally, bus lines could also be disposed diagonally as illustrated in FIG. 16. These lines 76, 80 respectively run along two of the natural axes of the hexagonal array and would therefore simplify addressing of subelements.

The number of access switches and row bus lines is determined by the size constraints and the application. For the purpose of disclosing one exemplary non-limiting implementation (shown in FIG. 13), a single access switch 30 for each subelement 32 and four row bus lines 34a–34d for each row of the array will be assumed. The second type of switch is a matrix switch 36, which is used to connect a connection point 42 of one subelement (see FIG. 17) to the connection point of a neighboring subelement. This allows an acoustical subelement 32 to be connected to a system channel through the integrated electronics associated with a neighboring acoustical subelement. This also means that an acoustical subelement may be connected to a system channel even though it is not directly connected via an access switch. While FIG. 13 shows three matrix switches 36 per subelement, it is also possible to have fewer than three to conserve area or to allow for switches which have lower on resistance and therefore have larger area. In addition, matrix switches can be used to route around a known bad subelement for a given array. Finally, while hexagonal subelements are shown, rectangular subelements are also possible and these might require fewer switches.

Figure 17:
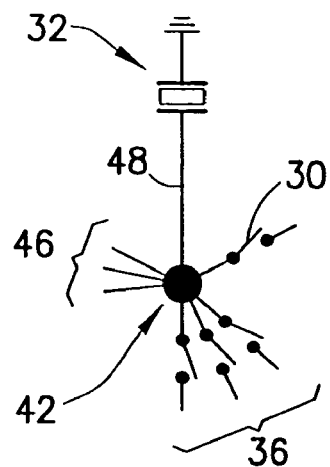
FIG. 17 is a drawing showing connections to a common connection point in the electronics associated with a particular acoustical subelement in accordance with the embodiment depicted in FIG. 13.

Referring to FIG. 17, each of the subelements comprises a common connection point 42 in the electronics associated with the acoustical subelement 32. This common connection point 42 electrically connects eight components in each subelement. The common connection point 42 connects the acoustic subelement or transducer 32 to the access switch 30 for that subelement, to the three matrix switches 36 associated with that subelement, and to the three matrix switches associated with three neighboring subelements via connections 46. A signal that travels through a matrix switch gets connected to the common connection point of the neighboring subelement.

FIG. 13 depicts how the switching network might work for a particular subelement. This is only an exemplary arrangement. A bus 34, which contains four row bus lines 34a through 34d, runs down the row of subelements 32. FIG. 13 shows only three subelements in this row, but it should be understood that other subelements in this row are not shown. The row bus lines of bus 34 are multiplexed to system channel bus lines of system channel bus 38 at the end of a row by means of multiplexing switches 40, which form a cross-point switching matrix. As seen in FIG. 13, each row bus line 34a–34d can be connected to any one of the system channel bus lines of bus 38 by turning on the appropriate multiplexing switch 40 and turning off the multiplexing switches that connect the particular row bus line to the other system channel bus lines. These multiplexing electronics can be off to the side and thus are not as restricted by size. FIG. 13 shows a fully populated cross-point switch. However, in cases wherein it is not necessary to have switches that allow every bus line to be connected to every system channel, a sparse cross-point switch can be used in which only a small subset of the system channels can be connected to a given bus line, in which case only some of switches 40 depicted in FIG. 13 would be present.

An access switch is so named because it gives a subelement direct access to a bus line. In the exemplary implementation depicted in FIG. 13, there are six other switch connections for each subelement. These connections take the form of matrix switches 36. A matrix switch allows a subelement to be connected to a neighboring subelement. While there are six connections to neighboring subelements for each subelement in this hexagonal pattern, only three switches reside in each subelement while the other three connections are controlled by switches in the neighboring subelements. Thus there is a total of four switches and associated digital addressing and control logic (not shown) in each subelement. This is just one exemplary implementation. The number of bus lines, the number of access switches, and the number and topology of the matrix switches could all be different, but the general concept would remain.

Figure 18:
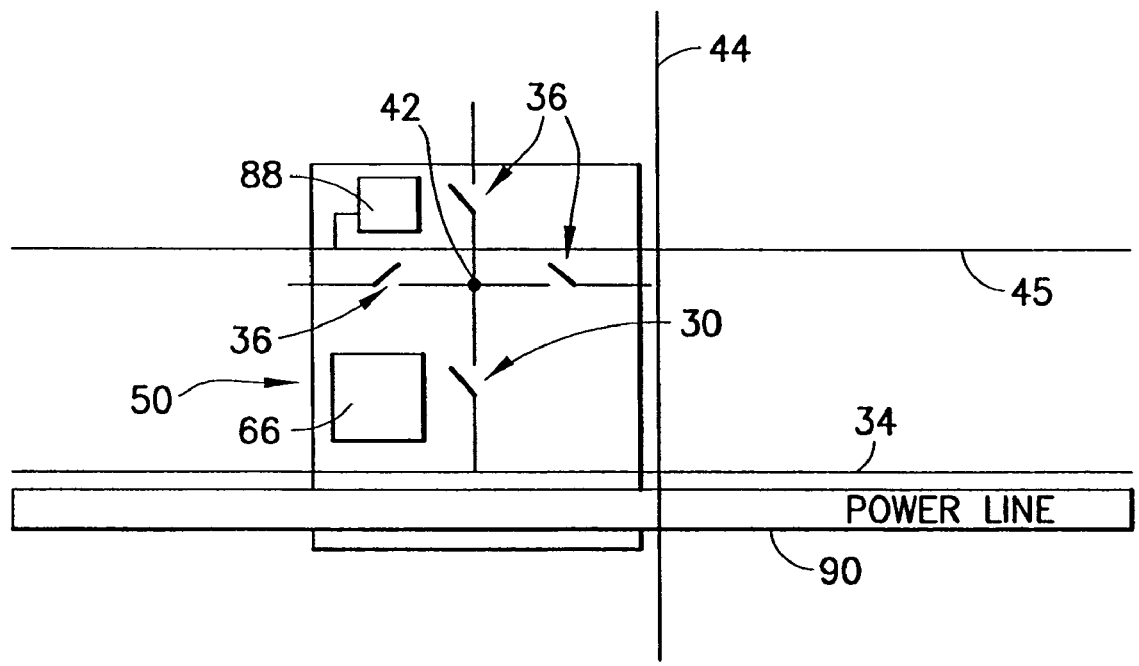
FIG. 18 is a drawing showing components of a representative unit switch cell built beneath and electrically connected to an acoustical subelement (not shown).

FIG. 18 shows some of the components of a representative unit switch cell built beneath and electrically connected (via connection point 42) to an acoustical subelement (not shown). The unit switch cell may be electrically coupled to the acoustical subelement via a metal pad 66 of the type depicted in FIG. 4. The unit switch cell comprises an access switch 30 that connects the connection point 42 to a bus line 34 and three matrix switches 36. These switches are of a type that have switch state memory for storing the current switch state. The unit switch cell further comprises latches 88 (only one of which is shown) for storing data representing the future switch states of the access switch 30 and the three matrix switches 36. The latches are standard CMOS memory elements, however, other memory elements such as EPROM, EEPROM, MRAM or MEMS could also be used. The future switch state data is received via a digital data bus 45 comprising multiple bus lines (only one bus line being shown in FIG. 18). In response to a write signal received via a control bus 44 comprising multiple bus lines (again only one bus line is shown), the future switch state data on data bus 45 is written into the latches 88. In response to a read signal received via the control bus 44 during a subsequent cycle, the switch state data is read out from the latches and converted (by logic not shown) into control signals that will change the states of the switches accordingly. These new switch states will be stored in the switch state memories of the switches. The latch 88 and switches 30 and 36 receive voltage supplies via power line 90.

Figure 19:
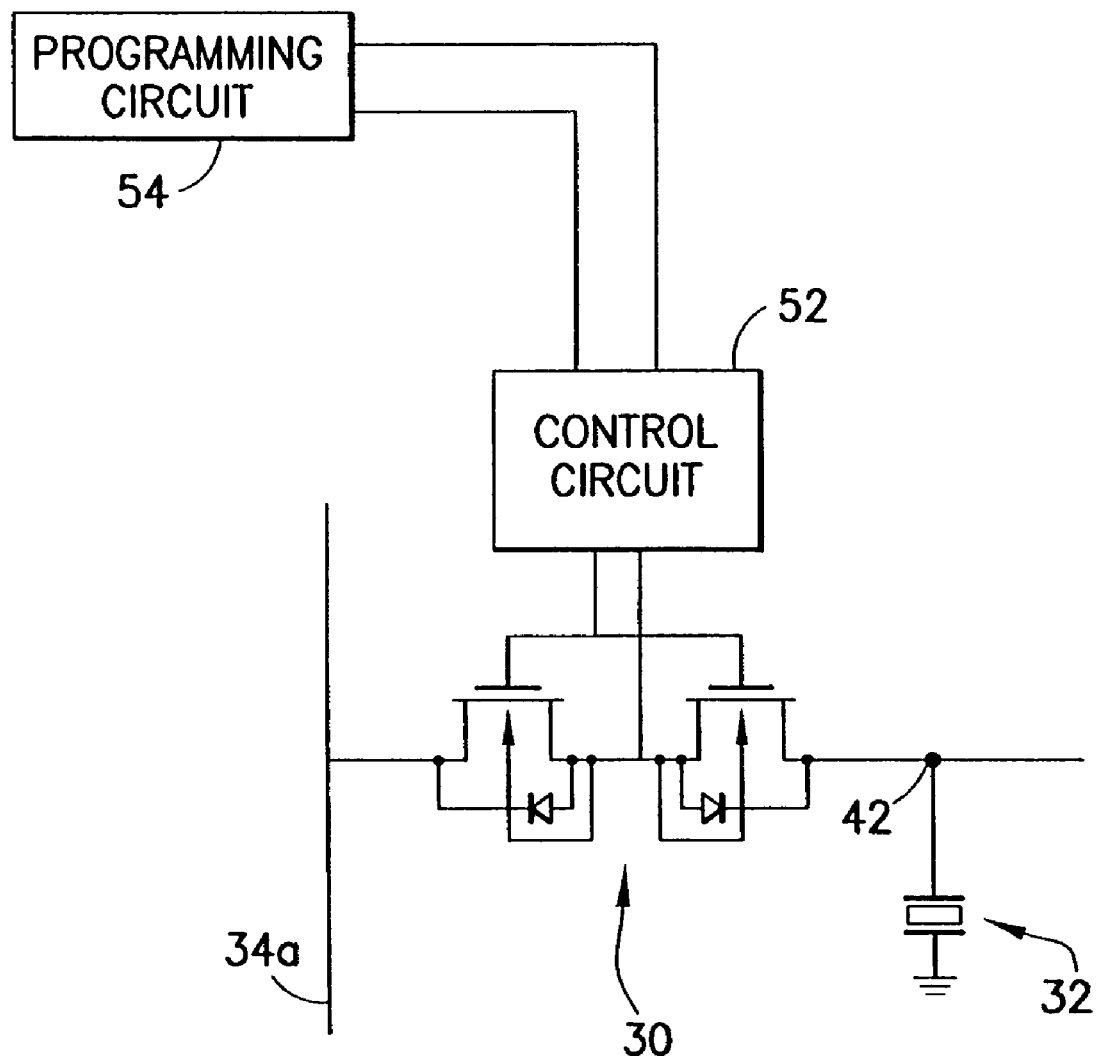
FIG. 19 is a drawing showing an access switch and circuitry for controlling the state of that access switch, as previously disclosed in U.S. patent application Ser. No. 10/248,968.

Although the access and matrix switches can be separately packaged components, it is possible to fabricate the switches within the same semiconductor substrate on which the MUT array is to be fabricated. The access and matrix switches may comprise high-voltage switching circuits of the type disclosed in U.S. patent application Ser. No. 10/248,968 entitled "Integrated High-Voltage Switching Circuit for Ultrasound Transducer Array". As seen in FIG. 19, each switch (e.g., an access switch 30) comprises two DMOS FETs that are connected back to back (source nodes shorted together) to allow for bipolar operation. Current flows through the switch terminals whenever both FETs are turned on. The states of the switches are controlled by a respective switch control circuit 52. The states of the switch control circuits are in turn dictated by outputs from a programming circuit 54, which programs the switch control circuits in accordance with a desired switching configuration. The programming circuit may be implemented using a view generator and address and data generator circuits of the types disclosed in U.S. patent application Ser. No. 10/978, 012 filed concurrently herewith and entitled "Method and Apparatus for Controlling Scanning of Mosaic Transducer Array", the disclosure of which is fully incorporated by reference herein. The switch control circuits may also be implemented in accordance with one of the embodiments disclosed in the latter patent application. The switches could be CMOS, DMOS, BiCMOS, BCDMOS, MEMS or any other highly integrated switching technology available currently or in the future.

FIG. 19 shows an acoustical subelement 32 connected to an access switch 30 via a common connection point 42. The six other lines that connect to the connection point 42 are not shown. For this example, the access switch 30 comprises the aforementioned pair of back-to-back DMOS FETs. The control circuit 52 turns the switch 30 on or off as a function of switch state data signals sent by the programming circuit 54. When access switch 30 is turned on, the acoustical subelement 32 (e.g., a subarray of interconnected cMUT cells) is connected to a row bus line 34a. For this configuration, the electronics associated with each acoustical subelement (i.e., the "unit switch cell") will comprise one access switch, three matrix switches, a respective control circuit for each of these four switches, and a respective conductor connecting the common connection point to the matrix switches of three neighboring subelements (not shown). Optionally, each unit switch cell also comprises latches for storing the future switch states of the switches in that unit switch cell, as disclosed in U.S. patent application Ser. No. 10/978,196, filed concurrently herewith. The addition of digital memory in the form of latches is useful in that it implements the requirement for fast transition of aperture patterns between successive transmit and receive operations.

Still referring to FIG. 19, the signal that travels from the acoustical subelement 32 to the row bus line 34a is the electrical receive signal. Here the receive signal is the electrical response generated by the acoustical subelement 32 when a sound pressure wave interacts with the transducer. The transmit signal, in which an electrical pulse is generated by the ultrasound system, travels from the row bus line 34a to the acoustical subelement 32. For a given channel, this electrical excitation pulse travels through a system channel bus line to a row bus line. The signal travels from the row bus line to the acoustical subelement through an access switch 30 and also travels to other subelements through the matrix switches (not shown in FIG. 19).

The number of switches that fit behind an acoustical subelement is limited. The size of the switch determines the on resistance of the switch and the smaller the switch the larger the on resistance. The delay and distortion caused by the switching increases as the switch on resistance increases. This means that there is a tradeoff between the number of switches behind an acoustical subelement and the delay introduced by those switches. One solution to that tradeoff involves reducing the number of switches to a small number while retaining as much flexibility as possible. This reduction is achieved by using matrix switches to allow acoustic subelements to be attached to a system channel through other subelements, and by limiting the number of access switches to a small number.

The bus lines that connect the access switches to the systems channels also take space in the electronics layer, so minimizing the number of bus lines is also beneficial. The number of unique channels that can be directly connected to acoustic subelements in the same row is determined by the number of bus lines. However, since the matrix switches allow subelements in one row to connect to subelements in other rows, the number of channels in a row is increased by the matrix switches. This allows the number of bus lines to be kept small, while still servicing a large number of channels. Of course, having more bus lines increases the flexibility but requires more space.

The use of matrix switches means that the number of access switches behind each subelement can be reduced. In the extreme case there is only one access switch for each subelement. However, if there is more than one bus line, a determination must be made as to which bus line each access switch should be connected. One solution is to stagger the connections so that the bus line connected to repeats every N subelements in a row, where N is a number determined by the requirement of minimum signal distortion as discussed below. Returning to FIG. 13, each subelement 32 in the row is connected to one of the row bus lines in the row bus 34 via a respective access switch 30. This pattern of staggered connections repeats every four subelements. The staggering allows more bus lines with fewer access switches and combined with the matrix switches, still allows for great flexibility as to which system channels can be connected to each subelement. Of course having more than one access switch per cell increases the flexibility of the connections but requires smaller switches with higher on resistance.

Figure 20:
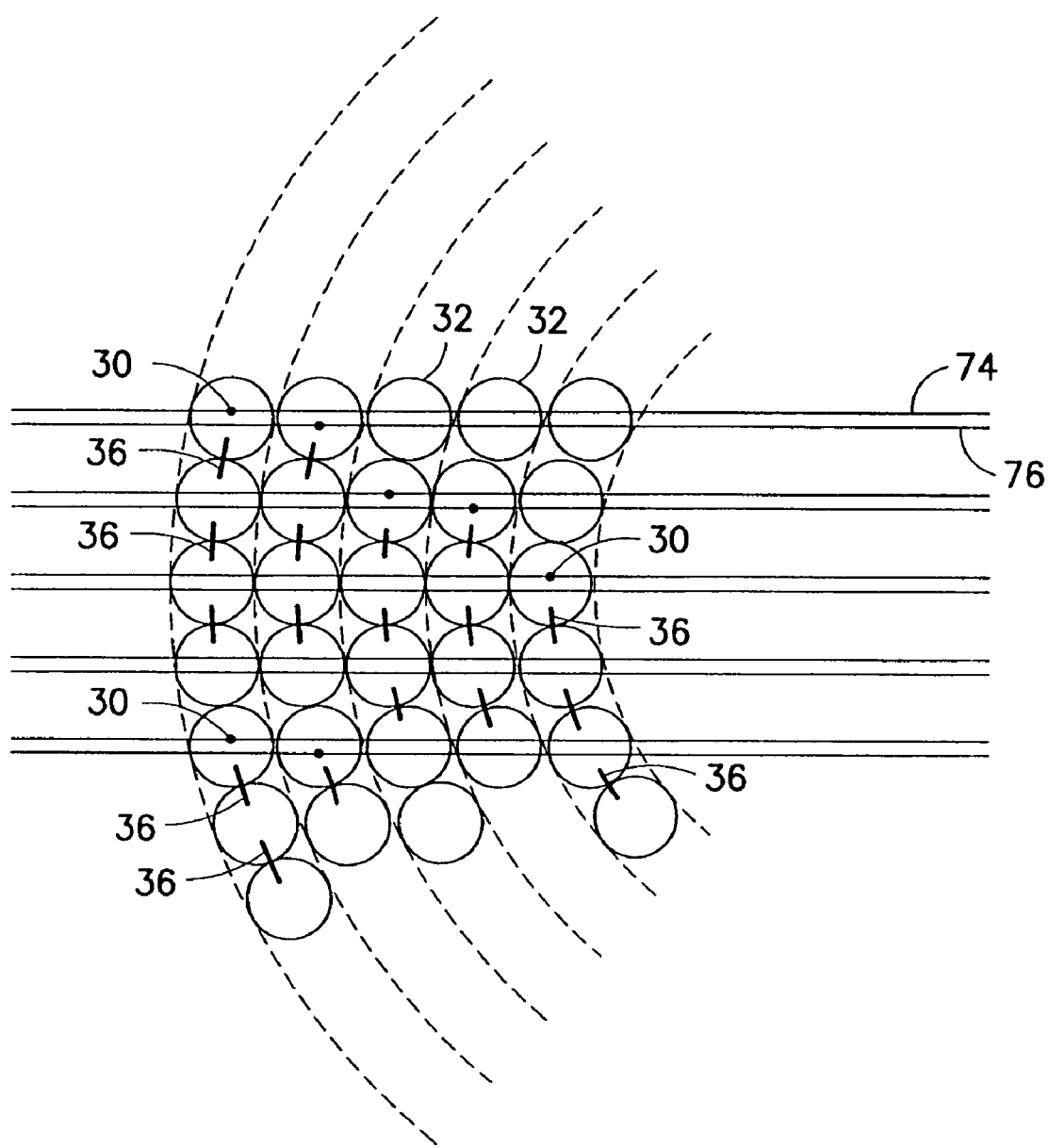
FIG. 20 is a drawing showing an arrangement of access and matrix switches for use with rings (portions of which are indicated by dashed arcs) with single subelement width that are packed close together. Access switches are indicated by solid dots; matrix switches are indicated by dashes.

Generally, the number of rows N after which the pattern repeats is determined by the maximum number of matrix switches which can be strung together while still maintaining adequate signal integrity. This number comes out of the understanding that the matrix switch resistance and cMUT capacitances together form an RC delay line with a time constant of delay which varies exponentially with the number of series taps N. Staggering the access switches on multiple row bus lines allows the number of elements that can be supported to be increased given the constraint of the delay line. As illustrated in FIG. 20, the worst case for the design occurs where rings (portions of which are indicated by dashed arcs) with single subelement width are packed close together. The vertical sections of the ring provide the worst case since bus lines 74, 76 in this design run horizontally. In the horizontal sections of the rings, one could just use a single access switch at every subelement since they would all be the same as the bus lines run parallel to the rings. In the vertical sections however, every row of subelements 32 is associated with a different bus line that is connected to a different system channel. Therefore, subelements spaced vertically in this area can only be supported using matrix switches 36, represented by dashes. In FIG. 20, there are two bus lines per row, and the pattern of access switches 30 (represented by dots) repeats every four rows subelements. At each row, two rings are supported by the two access switches and their associated string of subelements grouped with matrix switches. Since the pattern repeats after four rows, this particular architecture will support a maximum of 2×4=8 rings. In general for an array with M bus lines on each row and N taps for each string of subelements, a maximum of K system channels can be supported where K=M×N. Of course, most sections of the rings will be neither perfectly horizontal nor perfectly vertical. Therefore the task of the system designer is to optimize the array configuration at all points in the aperture under the constraints of the architecture. Various methods for optimizing such a switching configuration are disclosed in U.S. patent application Ser. No. 10/978,175, filed concurrently herewith and entitled "Optimized Switching Configurations for Reconfigurable Transducer Arrays".

In accordance with a further aspect of the invention, the metal routing between the sensor and electronics planes includes rerouting that allows use of an electronics chip or chips having an area larger than the area of the sensor array, as seen in FIG. 22. FIG. 22 depicts a plurality of transducer subelements 32 built on a substrate 94, with a pair of electronics chips 90A and 90B laminated to the bottom of the substrate 94, each chip comprising a respective plurality of unit switch cells 50. The metal routing 96 diverges, with the connections to the sensor plane being confined to an area smaller than the area of the electronics chips 90A and 90B.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A device comprising
a multiplicity of sensors arranged along a first set of substantially parallel lines in a first stratum;
a multiplicity of unit electronics cells arranged along a second set of substantially parallel lines in a second stratum; and
a multiplicity of electrical connections, each of said electrical connections electrically connecting a respective one of said unit electronics cells to a respective one of said sensors,
wherein each of said unit electronics cells comprises:
a respective plurality of switches for closing respective pathways to a respective connection point that is electrically connected to a respective sensor and that is not switchably disconnectable from said respective sensor; and
control circuitry for controlling the switch states of said switches.

2. The device as recited in claim 1, wherein each of said electrical connections comprises a respective bump made of electrically conductive material, anisotropic conductive paste (ACP), anisotropic conductive film (ACF), an electrically conductive polymer, a metallized bump, a vertical interconnect system, e.g., a z-axis interposer, a flexible printed circuit, or a metallized via.

3. The device as recited in claim 1, further comprising a layer of material disposed between said first and second strata, wherein each of said electrical connections comprises a respective metallized via in said layer of material.

4. The device as recited in claim 1, further comprising a multiplicity of bus lines, wherein at least one of said switches in each unit electronics cell is an access switch that connects the associated sensor with one of said bus lines when said access switch is turned on.

5. The device as recited in claim 4, wherein at least one of said switches in each unit electronics cell is a matrix switch that connects the sensor associated with a neighboring unit electronics cell to said one bus line via said access switch when said access switch and said matrix switch of each unit electronics cell are turned on.

6. The device as recited in claim 1, wherein even-numbered lines of said sensors are offset relative to odd-numbered lines of said sensors and distributed with the correct spacing to form a hexagonal grid of sensors.

7. The device as recited in claim 6, wherein even-numbered lines of said unit electronics cells are offset relative to odd-numbered lines of said electronics cells to form a hexagonal grid of unit electronics cells that generally matches said hexagonal grid of said sensors, and said multiplicity of electrical connections are also arranged in a hexagonal array.

8. The device as recited in claim 6, wherein said unit electronics cells are arranged in horizontal rows and vertical columns to form a rectangular grid of unit electronics cells, and said multiplicity of electrical connections are also arranged in a rectangular array with horizontal and vertical spacing that aligns with the hexagonal grid of sensors.

9. The device as recited in claim 1, wherein each of said sensors comprises a respective ultrasonic transducer subelement.

10. The device as recited in claim 9, wherein each of said ultrasonic transducer subelements comprises a respective multiplicity of capacitive micromachined ultrasonic transducer cells that are interconnected to each other and are not switchably disconnectable from each other.

11. The device as recited in claim 1, wherein each of said unit electronics cells comprises a respective plurality of memory devices for storing future switch states of said switches.

12. The device as recited in claim 1, wherein said multiplicity of sensors occupies about the same area as said multiplicity of unit electronics cells.

13. The device as recited in claim 1, wherein said multiplicity of sensors and said multiplicity of unit electronics cells are co-integrated on the same substrate.

14. The device as recited in claim 1, wherein said multiplicity of sensors are micromachined in or on a first substrate, and said multiplicity of unit electronics cells are integrated on a second substrate, said first and second substrates being arranged to form a stack.

15. The device as recited in claim 1, wherein said switches are CMOS switches.

16. The device as recited in claim 1, wherein said sensors are arranged in a hexagonal grid, and each of said unit electronics cells comprises three matrix switches for connecting each unit electronics cell to three adjacent unit electronics cells.

17. The device as recited in claim 1, wherein said sensors are arranged in a hexagonal grid, and each of said unit electronics cells comprises a respective pad made of electrically conductive material, each pad being electrically connected to a respective one of said electrical connections, said pads being arranged in a rectangular array.

18. A device comprising
a multiplicity of sensors built in or on a first substrate;
a multiplicity of unit electronics cells integrated in a second substrate disposed adjacent to and confronting said first substrate;
a multiplicity of bus lines supported by said second substrate; and a multiplicity of electrical connections disposed between said first and second substrates, each of said electrical connections electrically connecting a respective one of said unit electronics cells to a respective one of said sensors, wherein each of said unit electronics cells comprises a respective plurality of switches and a respective control circuit for controlling the switch states of said switches, each plurality of switches comprising an access switch that connects the associated sensor with one of said bus lines when said access switch is turned on, and a matrix switch that connects a sensor associated with a neighboring unit electronics cell to said one bus line via said access switch when said access switch and said matrix switch of the unit electronics cell are turned on.

19. The device as recited in claim 18, wherein each of said electrical connections comprises a respective bump made of electrically conductive material, said bumps being disposed between said first and second substrates.

20. The device as recited in claim 18, wherein each of said sensors comprises a respective ultrasonic transducer subelement.

21. The device as recited in claim 20, wherein each of said ultrasonic transducer subelements comprises a respective multiplicity of capacitive micromachined ultrasonic transducer cells that are interconnected to each other and are not switchably disconnectable from each other.

22. The device as recited in claim 18, further comprising a layer of material disposed between said first and second substrates, wherein each of said electrical connections comprises a respective metallized via in said layer of material.

23. The device as recited in claim 22, wherein said material of said layer is acoustic backing material.

24. The device as recited in claim 6, wherein said sensors are arranged in a hexagonal grid and said unit electronics cells are arranged in a hexagonal grid that generally matches said hexagonal grid of said sensors.

25. The device as recited in claim 6, wherein said sensors are arranged in a hexagonal grid and said unit electronics cells are arranged in a rectangular grid.

26. A device comprising:
a multiplicity of ultrasonic transducer subelements arranged in a first stratum, each subelement comprising a respective plurality of cMUT cells that are electrically interconnected with each other and are not switchably disconnectable from each other;
a multiplicity of unit CMOS electronics cells arranged along a second stratum that underlies said first stratum;
a multiplicity of bus lines; and
a multiplicity of electrical connections, each of said electrical connections electrically connecting a respective one of said unit CMOS electronics cells to a respective one of said ultrasonic transducer subelements, wherein each of said unit CMOS electronics cells comprises a respective plurality of switches and a respective control circuit for controlling the switch states of said switches, each plurality of switches comprising an access switch that connects the associated ultrasonic transducer subelement with one of said bus lines when said access switch is turned on, and a matrix switch that connects an ultrasonic transducer subelement associated with a neighboring unit CMOS electronics cell to said one bus line via said access switch when said access switch and said matrix switch of the unit CMOS electronics cell are turned on.

27. The device as recited in claim 26, wherein said ultrasonic transducer subelements are arranged in a hexagonal grid and said unit CMOS electronics cells are arranged in a rectangular grid.

28. The device as recited in claim 26, further comprising a layer of material disposed between said ultrasonic transducer subelements and said unit CMOS electronics cells, wherein each of said electrical connections comprises a respective metallized via in said layer of material.

29. The device as recited in claim 28, wherein said material of said layer is acoustic backing material.

30. The device as recited in claim 10, wherein each of said capacitive micromachined ultrasonic transducer cells comprises a top electrode and a bottom electrode connected to a respective unit electronics cell via respective vias.

31. The device as recited in claim 1, wherein said multiplicity of sensors occupies an area less than the area occupied by said multiplicity of unit electronics cells.

32. The device as recited in claim 21, wherein each of said capacitive micromachined ultrasonic transducer cells comprises a top electrode and a bottom electrode connected to a respective unit electronics cell via respective vias.

33. The device as recited in claim 18, wherein said first substrate has an area less than the area of said second substrate.

* * * * *